United States Patent [19]

Shin et al.

[11] 4,435,382

[45] Mar. 6, 1984

[54] ANHYDROUS ALCOHOLIC ANTIPERSPIRANT SUSPENSION COMPOSITION CONTAINING CERTAIN ALUMINUM OR ALUMINUM/ZIRCONIUM SALT GLYCINE COMPLEXES

[75] Inventors: Chung T. Shin, Livingston; Navin Geria, Elizabeth, both of N.J.

[73] Assignee: Bristol-Myers Company, New York, N.Y.

[21] Appl. No.: 168,925

[22] Filed: Jul. 14, 1980

[51] Int. Cl.$^3$ .......................... A61K 7/34; A61K 7/38
[52] U.S. Cl. ...................................... 424/66; 424/184; 424/357
[58] Field of Search ......................................... 424/66

[56] References Cited

U.S. PATENT DOCUMENTS

| | | | |
|---|---|---|---|
| 2,814,584 | 11/1957 | Daley | 424/66 |
| 2,814,585 | 11/1957 | Daley | 424/66 |
| 3,009,771 | 11/1961 | Grote et al. | 424/66 UX |
| 3,395,214 | 7/1968 | Mummert | 424/47 |
| 3,407,254 | 10/1968 | Siegal et al. | 424/66 |
| 3,792,068 | 2/1974 | Luedders et al. | 424/66 |
| 3,903,258 | 2/1975 | Siegal | 424/66 |
| 4,017,599 | 4/1977 | Rubino | 424/47 |
| 4,028,390 | 6/1977 | Rubino | 424/66 X |
| 4,053,581 | 10/1977 | Pader et al. | 424/68 |
| 4,065,564 | 12/1977 | Miles, Jr. et al. | 424/66 |
| 4,073,880 | 2/1978 | Pader et al. | 424/66 |

FOREIGN PATENT DOCUMENTS 1487812 10/1977 United Kingdom .................. 424/66

OTHER PUBLICATIONS

Todd et al., 1/1976, vol. 91, Cosmetics & Toiletries, pp. 29 to 32.

*Primary Examiner*—Dale R. Ore
*Attorney, Agent, or Firm*—Irving Holtzman; Gabriel P. Katona; George A. Mentis

[57] ABSTRACT

An antiperspirant composition of the suspension type comprising an anhydrous alcoholic vehicle having suspended therein one or more of the following astringent salt glycine complexes and a suspending agent: aluminum/zirconium/tetrachlorohydrate glycine complexes; aluminum/zirconium/trichlorohydrate glycine complexes; aluminum/zirconium/pentachlorohydrate glycine complexes; aluminum/zirconium/octachlorohydrate glycine complexes; and aluminum/sesquichlorohydrate glycine complexes. Composition may also contain a non-staining hydrophilic emollient and/or a non-polar emollient and/or a volatile emollient.

21 Claims, No Drawings

ANHYDROUS ALCOHOLIC ANTIPERSPIRANT SUSPENSION COMPOSITION CONTAINING CERTAIN ALUMINUM OR ALUMINUM/ZIRCONIUM SALT GLYCINE COMPLEXES

This invention relates to antiperspirant suspension compositions. More particularly, it concerns antiperspirant compositions in which the active antiperspirant materials are present in the form of essentially insoluble particles suspended in an essentially anhydrous liquid vehicle. This invention especially concerns antiperspirant suspension compositions of the so-called "roll-on" type; that is, compositions that are designed particularly for application by a roll-on dispenser.

A number of astringent salts are known in the prior art which are said to be effective antiperspirant materials. However, the degree of effectiveness, the long-lasting efficacy and the organoleptic qualities of the astringent salts are to a large extent dependent upon the form of the composition from which they are dispensed.

It has been suggested, for example, to prepare antiperspirant compositions for pump spray or roll-on application in which the active antiperspirant is present in solution in a vehicle which is primarily alcoholic vehicle (see U.S. Pat. No. 4,073,880). For this purpose, an alcohol soluble aluminum salt and/or complex is suggested as the active antiperspirant. Although solutions of the active antiperspirant materials are inclined to have effective antiperspirant activity, they are disadvantageous from other aspects. Thus, for example, they do not have the same long-lasting effect that is characteristic of suspension type products. Suspension type produces are therefore to be preferred because of their long-lasting effect. Moreover, the alcohol solution type products also tend to be organoleptically unsatisfactory in that they are inclined to be tacky when applied.

Antiperspirant roll-on preparations in the form of an oil-in-water emulsion or an aqueous alcoholic liquid that uses a variety of astringent salts as antiperspirant materials are also known in the prior art. These, however, have the disadvantage in that they go on wet and therefore, cause some discomfort.

It is also known in the prior art to prepare antiperspirant compositions of the suspension type which contain aluminum chlorohydrate as the active antiperspirant material. In addition, these compositions are known to contain a volatile silicone (cyclomethicone), alcohol, octyl palmitate, isopropyl palmitate, stearalkonium hectorite, propylene carbonate and fragrance. These products, however, have a high staining potential that, to a large extent, is probably due to the presence of the fatty acid ester emollients i.e. octyl palmitate and isopropyl myristate which are contained in these compositions in significant quantities. When an effort is made to reduce the staining portential of these products by removing the fatty acid esters, the suspension becomes unstable and the aluminum chlorohydrate becomes a gel.

It has now been found that an antiperspirant composition of the suspension type (and therefore of the long-lasting type) can be provided having the appropriate organoleptic properties which can be provided by combining in an essentially anhydrous alcoholic vehicle, certain specific aluminum salt-glycine complexes or aluminum zirconium salt-glycine complexes and a suspending agent. Moreover, these products are stable and quick drying and have a low potential for staining.

It is accordingly an object of this invention to prepare an antiperspirant composition of the suspension type useful as a roll-on preparation that is stable and long-lasting.

It is a further object of the present invention to provide an antiperspirant composition of the above type that is further characterized as not being tacky when applied and as being quick drying.

Although, according to the present invention, certain specific aluminum salt glycine complexes or certain aluminum zirconium salt glycine complexes form stable suspensions in an anhydrous alcoholic vehicle containing a suspending agent, some of these compositions are inclined to have an undesirable staining potential. It has been found that this can be eliminated by also incorporating in the composition a nonstaining hydrophilic emollient described in more detail below.

It is accordingly still a further object of this invention to provide an antiperspirant composition of the type set out in the above objects that is further characterized as having a low staining potential.

It is another object of this invention to provide a method for inhibiting perspiration in subjects by applying the compositions set out in the above objects.

Other and more detailed objects of this invention will be apparent from the following description and claims.

As previously mentioned, the benefits of the present invention are obtained through the use of certain specific complexes formed between certain aluminum salts and glycine, on the one hand, or certain aluminum/zirconium salts and glycine. The complexing of these salts with glycine alters the solubility of these salts in the essentially anhydrous alcoholic vehicle rendering the salts less soluble and therefore, more readily suspendible therein. By being more suspendible and therefore, less likely to go into solution in the liquid vehicle, the active materials are available for long-lasting activity.

Although applicants do not want to be bound by any theory, it is their belief that the longer lasting action exhibited by its suspension products can be explained as a type of "sustained release" activity. At any one time, a small portion of the active material is dissolved in the alcohol vehicle and is ready for acting immediately. The suspension active material which is the bulk of material is in a sense held in reserve and becomes active upon moisturization of the underarm area.

The particular astringent salt glycine complexes that may be employed in the present invention are selected from the group consisting of aluminum/zirconium/tetrachlorohydrate glycine complexes (e.g. Wickenol #E-369, Wickenol E-1363), aluminum/zirconium/trichlorohydrate glycine complexes (e.g. Reheis type 410 Micronized Powder), aluminum/zirconium/pentachlorohydrate glycine complexes, aluminum/zirconium/octachlorohydrate glycine complexes and aluminum/sesquichlorohydrate glycine complexes and mixtures thereof. The aluminum/zirconium chlorohydrates that are used in preparing the aforesaid mentioned glycine complexes can be prepared by mixing aluminum chlorohydrate with zirconium hydroxychloride. The glycine is then incorporated into these mixtures. In some cases, Al/Zr chlorohydrate also can be prepared by reacting aluminum and zirconium carbonate with hydrochloric acid. The glycine is then incorporated into these mixtures. In a typical process, Al/Zr chlorohydrate glycine complex solution is spray dried. In a preferred form of this invention, the molar ratio of Al/Zr in the aluminum/zirconium tetrachlorohydrate glycine complexes employed is from about 3:1 to about 4.5:1. In the case of the aluminum/zirconium trichlorohydrate glycine complex, the molar ratio of Al/Zr is also preferably about 3:1 to 4.5:1. The U.S. Pat. No. 3,792,068 to Luedders describes the preparation of Al/Zr chlorohydrate glycine complexes which may also can be used in the present invention.

The aluminum sesquichlorohydrate glycine complex that is employed in the present invention can be prepared by mixing aluminum chloride (e.g. aluminum chloride hexahydrate) with aluminum chlorhydroxide and then incorporating glycine in the mixture. In a typical process, aluminum chloride hexahydrate is added to a solution of aluminum chlorohydrate solution and the solution is mixed until clear. The glycine is added and then this solution is spray dried.

The aluminum sesquichlorohydrate glycine complexes that are useful for the purpose of the present invention are characterized by the fact that the molar ratio of aluminum to chloride will fall within the range of from about 0.78:1 to about 1.95:1 with the preferred range being in the range of from about 1.33:1 to about 1.79:1. The optimum results are obtained with aluminum sesquichlorohydrate glycine complexes in which the molar ratio of aluminum to chloride is in the range of from 1.39:1 to about 1.5:1.

The quantity of glycine that will be complexed with the astringent salts used herein will vary somewhat. Usually, this will be in the range of from about 5% to about 20% by weight based on the total weight of the astringent salt. The preferred range, however, is from about 7% to about 15% by weight of glycine based on the total weight of the astringent salt.

The following are the specifications of various glycine complexes that are useful for the present purposes:

| Aluminum/Zirconium/Tetrachlorohydrate Glycine (Wickenol #E-369) | | |
|---|---|---|
| | $Al_4ZrO(OH)_{10}Cl_4 \cdot NH_2CH_2COOH$ | |
| Test | Range | Preferred |
| Form @ 25° C. | Off White Powder | Off White Powder |
| % Aluminum as Al | 14.5–15.5% | 15.1–15.2% |
| % Zirconium as Zr | 14.49 max | 13.9–14.4% |
| Al:Zr atomic ratio | 3.4:1–3.8:1 | 3.66:1–3.57:1 |
| % Chloride | 17.0–18.5% | 17.5–17.6% |
| % Glycine | 10.5–13.5% | 11.8–13.0% |
| pH (15% aq.) | 3.7–4.1 | 3.8–3.95 |
| Metal:Chloride Atomic Ratio | 0.9:1–1.5:1 | 1.44:1 |
| Loss on Heating 16 Hrs. @ 105° C. | 6.0–9.0 | 7.8–8.6 |
| Particle Size | 100% thru 270 mesh 98.5% Max. thru 325 mesh | 100% 99+% |

| Aluminum/Zirconium/Tetrachlorohydrate Glycine low moisture (Wickenol E-1363) | |
|---|---|
| Test | Analysis |
| Form @ 25° C. | Lt. Yellow Powder |
| % Aluminum as Al | 15.6% |
| % Zirconium as Zr | 14.8% |
| Al:Zr atomic ratio | 3.56:1 |
| % Chloride | 17.9% |
| % Glycine | 12.1% |
| Iron as Fe | 43 ppm |
| Loss on Heating 16 Hrs. @ 105° C. | 5.3% |
| pH (15% aq.) | 3.75 |
| Particle size | 100% thru 325 mesh |

Aluminum/Zirconium/Trichlorohydrate Glycine Complex (Reheis Chemical Type 410 Micronized Powder

| -continued Regular | |
|---|---|

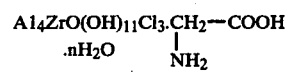

$$Al_4ZrO(OH)_{11}Cl_3 \cdot CH_2\text{—}COOH$$
$$\cdot nH_2O \quad\quad |$$
$$NH_2$$

| Analysis | Sample Results |
|---|---|
| % Aluminum as Al | 14.8% |
| % Zirconium as Zr | 14.0% |
| Al:Zr atomic ratio | 0.95:1 |
| % Chloride | 15.7% |
| % Glycine | 13.9% |
| pH (25% aq.) | 4.02 |
| Particle Size | |
| Residue on 325 mesh | 0.2% |
| Residue on 200 mesh | 0.0% |
| $H_2O$ 105° C. for 16 hrs. | 8.2% |

| Aluminum/Sesquichlorohydrate Glycine Complex | |
|---|---|

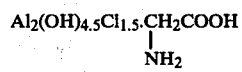

$$Al_2(OH)_{4.5}Cl_{1.5} \cdot CH_2COOH$$
$$|$$
$$NH_2$$

| Test | Range |
|---|---|
| % Aluminum as Al | 20.1–22.1% |
| % Chloride | 18.5–19.8% |
| Aluminum/Chloride Atomic Ratio | 1.39/1–1.50/1 |
| Glycine | 9.0–11.0 |
| pH (5% w/w suspension) | 3.9–4.3 |
| Particle Size | |
| % remaining on US 270 mesh | None |
| % remaining on US 325 mesh | 0.5% max. |
| Wt. loss at 105° C. for 16 hrs. | 9–15% |

The quantity of astringent salt complex that may be contained in the compositions of this invention may vary somewhat depending upon the results desired and other components contained in the composition. For the most part, this will be in the range of from about 14% to about 34% by weight based on the total weight of the composition.

Essentially anhydrous ethyl alcohol will usually be the major components of the liquid vehicle of the compositions of this invention. Alcohol SD 40 (anhydrous) that is commercially available will be quite suitable for this purpose. The amount of alcohol present may vary somewhat depending on the concentration of the various components as well as the particular materials selected. Ordinarily, however, it will constitute between about 10% or 20% to about 65% by weight based on the total weight of the composition, the preferred range being between about 20% to about 40%.

A third important component of these compositions are the suspending agents. A number of suspending agents well known in this art may be employed herein. The preferred agents in this class are the powdered silicon containing compounds that include such materials as the hydrated aluminum silicate clays, silica, hydrated silica, etc. A number of suspending agents of this type are available commercially. These include the so-called Bentone Clays (e.g. Bentone 27, Bentone 38; Bentone 34, NL Industries), fumed silicon dioxide (e.g. Cab-O-Sil M-5 Cabot), hydrated silica (Syloid).

The quantity of suspending agent that will be incorporated in the present composition will vary somewhat. Usually, this will fall within the range of from about 2% to about 5% by weight based on the total weight of the composition.

Not all suspending agents are of equal usefulness from the point of view of potential for staining. Thus, Bentone 38 and/or Cab-O-Sil M-5 are superior to Bentone 27. Furthermore, when high levels of alcohol are employed, more satisfactory products are obtained when the suspending agents are used in conjunction with both non-staining hydrophilic emollients and non-polar emollients described in more detail below.

As indicated above, in some instances, it is desirable to employ a non-staining hydrophilic emollient in the present compositions. A class of non-staining hydrophilic emollients that are especially useful herein are the polyoxypropylene, polyoxyethylene ethers of the aliphatic alcohols that can be described by the formula:

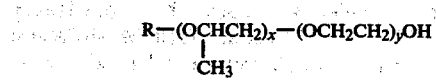

in which x and y are whole numbers. R is an aliphatic alcohol moiety having from 4° to 20 C atoms (e.g. butyl, cetyl, myristyl, stearyl). The value of x can range from 3 to 15 and the value of y can range from 2 to 50. The preferred range in the case of x it is 3 to 5 and for y it is 2 to 25. A material that is particularly suitable for the purposes of the present invention is a material of Formula II in which x has an average value of 5 and y has an average value of 20 and R is cetyl. A material of this type that is sold commercially is sold under the trade designation Procetyl AWS (Croda). Other commercially available materials which are suitable are Witconol APEM (PPG-3 Myreth-3), Witconol APES (PPG-9 Stearth-3), Standamul OXL (PPG-10 Cetearth-20), Procetyl AWS Modified (PPG-8 Ceteth-2), Ucon 50-HB-660 (PPG-12 Buteth-16), etc.

In general, non-staining hydrophilic emollients which are soluble and/or dispersible in water and soluble in alcohol are suitable. Aside from counteracting the staining potential of the non-polar emollient when employed, they also tend to improve the suspension stability and uniformity of viscosity over a variable temperature range.

The quantity of non-staining hydrophilic emollients that may be contained in the present composition may also vary over a range. Generally, it will constitute between 0 to about 25% by weight based on the total weight of the composition, with the preferred range being from about 3% to about 15% by weight on the same basis.

As an optional ingredient, the present compositions may contain a volatile emollient. This imparts superior organoleptic properties to the composition and is therefore used to advantage. The most widely known emollient of this character are the volatile silicones and are exemplified by Cyclomethicone. This is a cyclic dimethyl polysiloxane described in the CTFA Cosmetic Ingredient Dictionary, 2nd Edition, 1977, p. 71.

The quantity of volatile emollient that will be incorporated in the compositions of this invention will vary from 0 to about 40% by weight of the composition, the preferred upper range being about 25%. When the volatile emollient is used, it will be present in the range of from about 5% to 40% by weight based on the total weight of the composition and in the preferred range of from about 5% to about 25% by weight based on the total weight of the composition.

Another class of optional ingredients of the present composition is the non-polar emollients which are often employed herein as suspension stabilizers. The quantity of non-polar emollients that will be used will be in the range of from 0 to about 30% by weight based on the total weight of the composition. Best results are obtained when the non-polar emollient is used at a level in the range of from about 3% to about 25% by weight based on the total weight of the composition.

A variety of non-polar emollients may be used for the purposes of this invention. By way of example, mention may be made of fatty acid monoesters (isopropyl myristate), fatty acid diesters (Neobee M-20, dibutyl phthalate), branched fatty acid esters (2-ethyl hexyl pelargonate, 2-ethyl hexyl palmitate, 2-ethyl hexyl stearate, etc.), polyoxypropylene fatty ($C_4$–$C_{18}$) ethers (Witconol APS, Fluid AP), polysiloxanes, fatty alcohols (hexadecyl alcohol), etc. Suitable non-polar emollients that can be used herein are described in U.S. Pat. No. 3,968,203 column 3, lines 48 to 63.

When the non-polar emollients are employed, the potential for staining may tend to increase. To counteract this, it is advantageous to also incorporate in the compositions containing a non-polar emollient a non-staining hydrophilic emollient described above.

In addition to the components mentioned above, the present compositions may also include other ingredients that are conventionally contained in compositions of this character, these include things such as talc, Oat-Pro, DRY FLO, anti-bacterial agents, perfumes, coloring materials, etc.

As pointed out above, the selection of the particular astringent salt is very important in obtaining a satisfactory product according to the present invention. Thus, for example, if an attempt is made to employ aluminum chlorohydrate, severe product gellation is encountered in high alcohol content volatile silicone systems which contain Bentones or Cab-O-Sil M-5 as suspending agents. This is particularly true when the alcohol level exceeds a level of 20%.

Another interesting observation along these lines is the behavior of aluminum/zirconium/trichlorohydrate as compared with the corresponding glycine complex employed in the present invention. In the absence of glycine, the aluminum/zirconium/trichlorohydrate becomes exceedingly soluble in alcohol and discolors. This results in a gellation of the product which is obviously unacceptable. On the other hand, the aluminum/zirconium/trichlorohydrate in the presence of glycine (e.g. about 10% to about 15%) exhibited a diminished alcohol solubility with the consequent improvement in the stability profile of the products.

The moisture content of the astringent salt complexes employed in the present invention also appears to have a bearing on the overall suspension stability of the product. The lower "moisture content" complexes have a lower solubility in alcohol and demonstrate a better suspension stability. Furthermore, the products containing low moisture complexes also exhibit lower fabric staining potential.

The moisture content of the astringent salt complexes employed in the invention is best expressed in terms of the % loss in weight of the complex when heated at 105° C. for 16 hours. It has been found that good results are obtained when this percentage falls in the range of from about 4% to about 15%. In the table below, the preferred moisture ranges are given for the particular types of astringent complexes.

TABLE I

| Activities | Wt. loss at 105° C. 16 hours Range |
| --- | --- |
| Al/Zr tetrachlorohydrate glycine (Wickenol E-369) | 6–9 |
| Aluminum sesquichlorohydrate glycine | 9–15 |
| Al/Zr tetrachlorohydrate glycine (Wickenol E-1363) | 4–6 |
| Al/Zr trichlorohydrate glycine | 4–9 |

The following Examples are to further illustrate the present invention. It is to be understood, however, that the invention is not limited thereto.

EXAMPLE 1

Preparation of Aluminum Sesquichlorohydrate Glycine

| Ingredients | % by Wt. |
| --- | --- |
| Aluminum chloride hexahydrate (50% aq. sol) | 16.32 |
| Aluminum chlorhydroxide (50% aq. sol) | 73.43 |
| Glycine | 10.00 |
| Magnesium stearate | 0.25 |
| | 100.00 |

Procedure

A. The aluminum chloride hexahydrate is added to the 50% aluminum chlorhydroxide solution and mixed until clear, then the glycine and magnesium stearate are added and mixed into the solution.

B. The resulting mixture is spray dried, using a Bowen flat bottom drier having a diameter of 18 feet, under the following conditions:

| Inlet temperature | 350° F. |
| --- | --- |
| Outlet temperature | 140° F. |
| Feeding rate | 85 ± 5 gal/hr |

The resulting spray dried powder mix had a moisture content of 1.0%. This was determined by extracting the moisture using acetone from a sample of the dried product and then analyzing the water content of the extract using gas chromatography.

C. The dried powder is then ground in a jet mill and the resulting fine powder is screened through a 325 mesh sieve (44 microns) from which an active antiperspirant mix having uniform particle size is obtained.

Following the procedure of Example 1, dried antiperspirant powder mixes can be prepared from aqueous solutions containing Al/Cl molar ratios as follows:

| | Ex. 1A | Ex. 1B | Ex. 1C |
| --- | --- | --- | --- |
| Molar ratio Al/Cl | 1:1 | 1.5:1 | 1.79:1 |
| % by wt. aluminum chloride hexahydrate | 19.09 | 7.67 | 2.51 |
| % by wt. aluminum chlorhydroxide (50% aq. sol) | 70.91 | 87.33 | 95.49 |
| % by wt. glycine | 9.59 | 4.50 | 1.50 |
| % by wt. magnesium stearate | 0.50 | 0.50 | 0.50 |

EXAMPLE 2

Staining Test

The following laboratory staining test was used to evaluate staining potential of various formulations described below.

Procedure

"Hanes" white T-shirts were cut into 6"×8" swatches. Test material was applied by pipetting one gram of liquid product and spreading the product onto each of two 1"×6" strips across the fabric. The product was spread evenly to cover the entire 1"×6" area. Swatches were placed at 100° F. and 80–85% R.H. for 18–24 hours and laundered in a Sears Kenmore Heavy Duty Washer, Model 29921 set at Warm Wash/Warm Rinse (105° F. water), wash and second rinse, cotton white settings. The detergent manufacturer's directions were followed as closely as possible, which were consistent with AATCC test method 124-1978. On the average, 50 grams (¾ cup) of TIDE detergent were added to a 1.0 to 1.5 Kg load and 11.5 gallons (Ex. low setting) of water. Depending on load size, the amount of water (machine setting) and amount of detergent used was varied to insure AATCC test conditions (4.4–4.7 g. detergent/gallon of water, 42–54 g. detergent/Kg load).

Swatches were dried in a Sears Kenmore Automatic Dryer set at automatic cycle, cotton sturdy setting.

Ten test cycles were run for the suspension roll-on products.

Samples were evaluated visually for stains by at least two judges. The coding system for degree of stain in this study was as follows:

| Degree of Stain | Comments |
| --- | --- |
| None | No stain observable |
| Very slight | Barely perceptible |
| Very slight to slight | Average of very slight & slight |
| Slight | Obvious, undesirable; acceptable |
| Slight to moderate | Borderline, acceptable |
| Moderate | Unacceptable |
| Moderate to heavy | Unacceptable |
| Heavy | Unacceptable |

EXAMPLE 3

Formula BA 1746-24

| | % w/w |
| --- | --- |
| Bentone 38 | 1.50 |
| Cab-O-Sil M-5[1] | 1.00 |
| Alcohol SD 40, anhydrous | 49.05 |
| Cyclomethicone 7207 | 20.65 |
| Al/Zr tetrachlorohydrate glycine E-1363 | 12.00 |
| ACH BMS II[2] | 12.00 |
| Dibutyl phthalate | 3.80 |
| | 100.00 | after 10 applications & washings - slight staining
[1]Fumed silicon dioxide
[2]Aluminum sesquichlorohydrate glycine complex

| Ingredients | Ex. 4 BA 1746-66 % w/w | Ex. 5 FN 1624-84 % w/w | Ex. 6 BA 1746-77 % w/w |
| --- | --- | --- | --- |
| Bentone 38 | 1.50 | 1.50 | 1.50 |

-continued

| Ingredients | Ex. 4 BA 1746-66 % w/w | Ex. 5 FN 1624-84 % w/w | Ex. 6 BA 1746-77 % w/w |
|---|---|---|---|
| Cab-O-Sil M-5 | 1.00 | 1.00 | 1.00 |
| Alcohol SD 40 anhydrous | 49.05 | 49.05 | 49.05 |
| Cyclomethicone 7207 | 21.15 | 21.15 | 21.15 |
| PPG-8 Ceteth-2 | 3.00 | — | — |
| PPG-5 Ceteth-20 | — | — | 3.00 |
| ACH BMS II | 14.00 | 14.00 | 14.00 |
| Al/Zr tetrachlorohydrate glycine E-1363 | 10.00 | 10.00 | 10.00 |
| Perfume | 0.30 | 0.30 | 0.30 |
| Ucon 50 HB 660 | — | 3.00 | — |
| | 100.00 | 100.00 | 100.00 | after 10 applications & washings - no staining

| Ingredients | Ex. 7 BA 1746-78 % w/w | Ex. 8 BA 1746-88 % w/w | Ex. 9 BA 1746-38 % w/w |
|---|---|---|---|
| Bentone 38 | 2.50 | 2.50 | 2.50 |
| Bentone 27 | 1.00 | 1.00 | 1.00 |
| Cab-O-Sil M-5 | 1.50 | 1.50 | 1.50 |
| Alcohol SD 40 anhydrous | 51.42 | 55.92 | 55.92 |
| PPG-5 Ceteth-20 | 3.00 | — | — |
| PPG-8 Ceteth-2 | 1.50 | — | — |
| PPG-14 Butyl ether | 15.00 | 15.00 | 15.00 |
| Al/Zr tetrachlorohydrate glycine E 1363 (low moisture) | 10.00 | 10.00 | 10.00 |
| ACH BMS II | 14.00 | 14.00 | — |
| Perfume | 0.08 | 0.08 | 0.08 |
| | 100.00 | 100.00 | 100.00 |
| After 10 applications | no staining | slight staining | moderate staining |

| Ingredients | Ex. 10 Formula 1939 % w/w | Ex. 11 BQ 1809-24 % w/w | Ex. 12 BQ 1809-25 % w/w |
|---|---|---|---|
| Bentone 38 | 1.30 | 1.30 | 1.30 |
| Bentone 27 | 0.50 | 0.50 | 0.50 |
| Cab-O-Sil M-5 | 1.00 | 1.00 | 1.00 |
| Alcohol SD 40 anhydrous | 47.96 | 44.96 | 44.96 |
| Cyclomethicone 7207 | 24.94 | 24.94 | 24.94 |
| PPG-8 Ceteth-2 | — | 3.00 | — |
| PPG-5 Ceteth-20 | — | — | 3.00 |
| Al/Zr tetrachlorohydrate glycine E-1363 (low moisture) | 10.00 | 10.00 | 10.00 |
| ACH BMS II | 14.00 | 14.00 | 14.00 |
| Perfume | .30 | .30 | .30 |
| | 100.00 | 100.00 | 100.00 |

EXAMPLE 13

BA 1746-9

| | % w/w |
|---|---|
| Bentone 38 | 1.50 |
| Cab-O-Sil M-5 | 1.50 |
| Alcohol SD 40, anhydrous | 48.55 |
| Cyclomethicone 7207 | 17.35 |
| PPG-8 Ceteth-2 | 3.00 |
| Dibutyl phthalate | 3.80 |
| ACH BMS II | 24.00 |
| Perfume | 0.30 |
| | 100.00 |

| Ingredients | Ex. 14 BA 1746-75 % w/w | Ex. 15 BA 1746-74 % w/w |
|---|---|---|
| Bentone 38 | 2.50 | 2.50 |
| Bentone 27 | 1.00 | 1.00 |
| Cab-O-Sil M-5 | 1.50 | 1.50 |
| Alcohol SD 40, anhydrous | 51.42 | 52.92 |
| PPG-5 Ceteth-20 | 3.00 | 3.00 |
| PPG-8 Ceteth-2 | 1.50 | — |
| Fluid AP[3] | 15.00 | 15.00 |
| Al/Zr tetrachlorohydrate glycine E-1363 | 24.00 | 24.00 |
| Perfume | 0.08 | 0.08 |
| | 100.00 | 100.00 |

[3]Fluid AP - PPG-14 Butyl Ether

| Ingredients | Ex. 16 BA 1573-22 % w/w | Ex. 17 BA 1573-23 % w/w |
|---|---|---|
| Bentone 27 | 1.20 | 1.20 |
| ACH BMS II | 24.00 | 24.00 |
| Ucon 50 HB 660 | 22.50 | — |
| Procetyl AWS | — | 22.50 |
| Fluid AP | 7.50 | 7.50 |
| Alcohol SD 40, anhydrous | 25.84 | 20.84 |
| Cyclomethicone 7207 | 18.76 | 23.76 |
| Perfume | 0.20 | 0.20 |
| | 100.00 | 100.00 |

EXAMPLE 18

BA 1810-6

| Ingredients | % w/w |
|---|---|
| Bentone 38 | 2.50 |
| Bentone 27 | 1.00 |
| Cab-O-Sil M-5 | 1.50 |
| Fluid AP | 25.00 |
| Cyclomethicone 7207 | 20.00 |
| Procetyl AWS | 6.00 |
| Alcohol SD 40, anhydrous | 19.92 |
| Wickenol E-1363 | 10.00 |
| ACH BMS II | 14.00 |
| Perfume | 0.08 |
| | 100.00 |

EXAMPLE 19

BA 1810-10

| Ingredients | % w/w |
|---|---|
| Bentone 38 | 2.50 |
| Bentone 27 | 1.00 |
| Cab-O-Sil M-5 | 1.50 |
| Fluid AP | 25.00 |
| Cyclomethicone 7207 | 20.00 |
| Procetyl AWS | 6.00 |
| Alcohol SD 40, anhydrous | 19.92 |
| Al/Zr trichlorohydrate glycine type 410 | 10.00 |
| ACH BMS II | 14.00 |
| Perfume | 0.08 |

EXAMPLE 20

Formula 1901

| Ingredients | % w/w |
|---|---|
| Bentone 27 | 2.10 |
| Wickenol E-369 | 24.00 |
| Cab-O-Sil M-5 | 1.50 |
| Cyclomethicone 7207 | 24.85 |
| Alcohol SD 40, anhydrous | 47.47 |
| Perfume | .08 |
| | 100.00 |

It has been found that high alcoholic suspension roll-on such as Formula 1901 showed significantly higher staining potential than low or non-alcoholic suspension roll-on. However, addition of polyoxyethylene polyoxypropylene fatty alcohol ether reduced significant staining potential.

It has also been found that aluminum sesquichlorohydrate glycine showed significantly lower staining potential than Al/Zr tetrahydrate glycine formula. For example, BA 1746-38 containing 24% Al/Zr salt E-1363 showed moderate staining, but addition of 14% ACH BMS II replacing Al/Zr salt E-1363 made formula BA 1746-88 slight staining. BA 1746-78 containing non-staining emollients PPG-5 Ceteth-20 and PPG-8 Ceteth-2 eliminated staining potential.

Although the invention has been described with reference to specific forms thereof, it will be understood that many changes and modifications may be made without departing from the spirit of this invention.

What is claimed is:

1. A roll-on antiperspirant suspension composition adapted to be dispensed from a roll-on dispenser comprising an anhydrous ethyl alcohol vehicle containing an effective amount of a suspending agent and an antiperspirant effective amount of an astringent salt glycine complex suspended in said alcoholic vehicle, said complex being selected from the group consisting of aluminum/zirconium/tetrachlorohydrate glycine complexes; aluminum/zirconium/trichlorohydrate glycine complexes; aluminum/zirconium/pentachlorohydrate glycine complexes; aluminum/zirconium/octachlorohydrate glycine complexes; and aluminum/sesquichlorohydrate glycine complexes and mixtures of said complexes; said composition containing from about 20% to about 65% by weight of anhydrous ethyl alcohol.

2. A composition according to claim 1 also including a non-staining hydrophilic emollient.

3. A composition according to claim 2 in which said non-staining hydrophilic emollient is a polyoxypropylene, polyoxyethylene ether of an aliphatic alcohol of the formula:

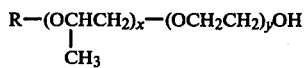

$$R-(OCHCH_2)_x-(OCH_2CH_2)_yOH$$
$$|$$
$$CH_3$$

in which x and y are whole numbers; R is an aliphatic alcohol moiety having from 4 to 20 C atoms; x has a value in the range of from 3 to about 15 and y has a value in the range of from about 2 to about 50.

4. A composition according to claim 2 also including a non-polar emollient.

5. A composition according to claim 3 also including a non-polar emollient.

6. A composition according to claim 5 wherein said non-polar emollient is selected from the group consisting of faty acid monoesters, fatty acid diesters, branched fatty acid esters and polyoxypropylene fatty ($C_4$–$C_{18}$) ethers, polysiloxanes, fatty alcohols and mixtures thereof.

7. A composition according to claim 1 including a volatile emollient.

8. A composition according to claim 7 in which said volatile emollient is a volatile silicone.

9. A composition according to claim 2 also including a volatile emollient.

10. A composition according to claim 9 in which the volatile emollient is a volatile silicone.

11. A composition according to claim 5 also containing a volatile emollient.

12. A composition according to claim 11 in which said volatile emollient is a volatile silicone.

13. A composition according to claim 6 also containing a volatile emollient.

14. A composition according to claim 13 in which said volatile emollient is a volatile silicone.

15. A composition according to claim 1, 2, 3, 4, 5, 6, 7, 8, 9, 10, 11, 12, 13 or 14 in which the various ingredients are present within the following ranges:

| | % by weight |
|---|---|
| (a) astringent salt glycine complex | from about 14 to about 34 |
| (b) suspending agent | from about 2 to about 5 |
| (c) non-staining hydrophilic emollient | from about 0 to about 25 |
| (d) non-polar emollient | from about 0 to about 30 |
| (e) volatile emollient | from about 0 to about 25. |

16. A composition according to claim 2 or 3 in which the various ingredients are present within the following ranges:

| | % by weight |
|---|---|
| (a) astringent salt glycine complex | from about 14 to about 34 |
| (b) suspending agent | from about 2 to about 5 |
| (c) non-staining hydrophilic emollient | from about 3 to about 25. |

17. A composition according to claim 4, 5, or 6 in which the various ingredients are present within the following ranges:

| | % by weight |
|---|---|
| (a) astringent salt glycine complex | from about 14 to about 34 |
| (b) suspending agent | from about 2 to about 5 |
| (c) non-staining hydrophilic emollient | from about 3 to about 25 |
| (d) non-polar emollient | from about 3 to about 25. |

18. A composition according to claim 7 or 8 in which the various ingredients are present within the following ranges:

|  | % by weight |
|---|---|
| (a) astringent salt glycine complex | from about 14 to about 34 |
| (b) suspending agent | from about 2 to about 5 |
| (c) volatile emollient | from about 5 to about 40. |

19. A composition according to claim 9 or 10 in which the various ingredients are present within the following ranges:

|  | % by weight |
|---|---|
| (a) astringent salt glycine complex | from about 14 to about 34 |
| (b) suspending agent | from about 2 to about 5 |
| (c) non-staining hydrophilic emollient | from about 3 to about 25 |
| (d) volatile emollient | from about 5 to about 40. |

20. A composition according to claim 11, 12, 13 or 14 in which the various ingredients are present within the following ranges:

|  | % by weight |
|---|---|
| (a) astringent salt glycine complex | from about 14 to about 34 |
| (b) suspending agent | from about 2 to about 5 |
| (c) non-staining hydrophilic emollient | from about 3 to about 25 |
| (d) non-polar emollient | from about 3 to about 25 |
| (e) volatile emollient | from about 5 to about 40. |

21. A process for inhibiting the flow of perspiration which comprises applying to the underarm of a subject an effective amount of the composition of claim 1, 2, 4, 7, 9 or 11.

* * * * *